(12) United States Patent
Wong et al.

(10) Patent No.: US 6,306,371 B1
(45) Date of Patent: Oct. 23, 2001

(54) COLOR STABLE SILVER ZEOLITE CONTAINING DENTIFRICE COMPOSITIONS

(75) Inventors: Mike Wong, Plainsboro; Prem Sreenivassan, Westfield; Suryakant Patel, Bridgewater; Nuran Nabi, Cranbury; John C. Brahms, Piscataway, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/506,605

(22) Filed: Feb. 18, 2000

(51) Int. Cl.[7] .............................. A61K 7/16; A01N 59/16; C08K 3/34; C01B 33/28; B01D 39/08
(52) U.S. Cl. ........................... 424/49; 424/618; 423/118; 428/323
(58) Field of Search .......................................... 424/49.58

(56) References Cited

U.S. PATENT DOCUMENTS

| | | | | |
|---|---|---|---|---|
| 4,775,585 | * | 10/1988 | Hagiwara et al. | 428/323 |
| 4,911,898 | * | 3/1990 | Hagiwara et al. | 423/118 |
| 4,911,899 | * | 3/1990 | Hagiwara et al. | 423/118 |
| 6,071,542 | * | 6/2000 | Tanimoto et al. | 424/618 |

FOREIGN PATENT DOCUMENTS

| | | | |
|---|---|---|---|
| 2443775 | * | 11/1991 | (GB) . |
| 93/24103 | * | 10/1993 | (WO) . |
| 99/44570 | * | 10/1999 | (WO) . |

* cited by examiner

*Primary Examiner*—Shep K. Rose
(74) *Attorney, Agent, or Firm*—Paul Shapiro

(57) ABSTRACT

An oral antiplaque composition comprising an orally acceptable vehicle and an effective antiplaque amount of silver zeolite and a stabilizing amount of a chloride salt.

7 Claims, No Drawings

COLOR STABLE SILVER ZEOLITE CONTAINING DENTIFRICE COMPOSITIONS

BACKGROUND OF THE INVENTION

1. Field of the Invention

This invention relates to storage stable antiplaque oral composition containing a silver zeolite compound which exhibits antibacterial efficacy against plaque causing oral bacteria.

2. The Prior Art

Dental plaque is a soft deposit which forms on teeth as opposed to calculus which is a hard calcified deposit on teeth. Unlike calculus, plaque may form on any part of the tooth surface, particularly at the gingival margin. Hence, beside being unsightly, it is implicated in the occurrence of gingivitis.

It is difficult to predict the efficacy of antibacterial agents when incorporated in oral compositions. For example, cationic antibacterial materials such as chlorhexidine, benzthonium chloride and cetyl pyridinium chloride have been used by the art as antibacterial antiplaque agents in oral compositions. However, such agents are generally not effective when there is also present anionic surfactants which surfactants are required for the effective performance of oral compositions such as toothpaste. Nonionic antibacterial materials are compatible with anionic ingredients in oral compositions and nonionic halogenated hydroxydiphenyl ethers such as Triclosan have been effectively employed in oral compositions as antiplaque agents when admixed with neutral materials such as humectants, abrasives and thickeners used in the formulation of oral compositions. Notwithstanding the antiplaque efficacy of Triclosan, there is a continuing interest in the oral composition field for such agents which are compatible with anionic surfactants present in such compositions.

Silver zeolite, is an antibacterial a compound used in products such as toothbrushes, clothing, medical devices, and kitchen cleaners. One main disadvantage of silver zeolite is that it causes discoloration (yellowing/browning) when present in products which are exposed to the environment. In dental products which contain silver zeolite, the silver ion is easily oxidized when exposed to air and light at room and elevated temperatures and forms a discolored precipate in the presence of anionic surfactants such as sodium lauryl sulfate (SLS) which substantially diminishes the acceptability of the product consumers.

Various means have been proposed by the art to overcome the discoloration problem have significant disadvantages. The silver zeolite containing product can be placed in air-tight and non-transparent packaging. This is not practical for most products because of cost constraints. Attempts to eliminate the presence of anionic surfactants such as SLS on toothpaste products is not practical as such elimination materially degrades the foaming and cleaning functionality of the product. Attempts to add colors and pigments such as titanium dioxide to mask the discoloration has limited success due to the continued presence of discoloration or "dulling" effects caused by the oxidation of silver ion.

SUMMARY OF THE INVENTION

In accordance with the present invention there is provided an antiplaque oral composition comprising an orally acceptable vehicle, an effective antiplaque amount of silver zeolite and a stabilizing amount of a soluble chloride, acetate or citrate salt. As will hereinafter be disclosed by the addition of low concentrations of salts such as sodium chloride a dentifrice can be formulated with both sodium lauryl sulfate and silver zeolite which does not undergo discoloration when exposed to environmental conditions. The dentifrice will not brown over a period of time at both room and accelerated temperature. In addition, direct air an sunlight exposure have no discoloration effect on the dentifrice.

DETAILED DESCRIPTION OF THE PREFERRED EMBODIMENTS

Silver zeolite compounds useful in the practice of the present invention are known to the art and are more fully describe in U.S. Pat. No. 4,938,958, U.S. Pat. No. 4,911,898, U.S. Pat. No. 4,775,585 and U.S. Pat. No. 4,525,410. The silver zeolite compounds are natural or synthetic zeolite particles retaining silver metal ions at the ion-exchangeable sites thereof. The silver ion is present in the zeolite typically at a concentration of about 0.2 to about 2.5% by weight and preferably about 0.3 to about 1% by weight.

Zeolite is generally aluminosilicate having a three-dimensionally grown skeleton structure and is generally shown by $X_{2/n}$ O—$Na_2O$—$Al_2O_3$-$2SiO_2 \cdot ZH_2O$, wherein X represents an ion-exchangeable metal ion, which is usually the ion of a monovalent or divalent metal; n corresponds to the valence of the metal; and Z is the number of water of crystallization. Various kinds of zeolites having different component ratio, fine pore diameter, and specific surface area are known and are available commercially.

As an example of the prior art concerning bactericidal silver zeolite compounds, U.S. Pat. No. 4,911,898 discloses bactericidal zeolite particle retaining silver metal ions having bactericidal properties at ion-exchangeable sites of the zeolite. The silver zeolite compound is prepared by contacting the zeolite with a solution of a water soluble silver salt, the silver ion of which has bactericidal properties thereby exchanging with the silver ion from the solution, the a concentration of the silver salt in the solution being sufficiently low to prevent deposition of silver compounds onto the zeolite and wherein the contacting is repeated until a substantial amount of the ion exchange capacity of the zeolite is reached.

Examples of water soluble salts which will impart color stabilization to oral compositions containing silver zeolite compounds include water soluble chloride salts such a sodium chloride, calcium chloride, potassium chloride, zinc chloride and strontium chloride and salts that combine with silver (ion) to form low water soluble salts such as acetates and citrates as for example calcium acetate and potassium and sodium citrate.

Salts that have been found not to be effective as color stabilizing agents are those that release anions that will combine with silver cations to form bromide, carbonate, oxide, phosphate and nitrate salts.

The silver zeolite compound is incorporated in oral compositions of the present invention in a non-toxic, effective antiplaque amount, typically in a range of about 0.5 to about 5% and preferably about 2.0 to about 4.0% by weight whereby 0.03 to about 3% by weight and preferably 0.3 to about 1% by weight silver ion is released by the silver zeolite compound. The color stabilizing salt is incorporated in the oral composition at a concentration of about 0.03 to about 3% and preferably 0.1 to about 1% by weight.

Surfactants are used in the compositions of the present invention to achieve increased prophylactic action and assist in achieving thorough and complete dispersion of the oral composition ingredients and are present in the oral composition at a concentration of about 0.5 to about 5% by weight and preferably about 1 to about 30% by weight throughout the oral cavity. The surfactant material is preferably anionic, suitable examples which include water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals and alkoyl taurines, and the like. Examples of the last mentioned amides and taurates are N-lauroyl sarcosine, and the sodium, potassium and ethanolamine salts of N-lauroyl, N-myristoyl, or N-palmitoyl sarcosine which should be substantially free from soap or similar higher fatty acid material as well as N-methyl-N-cocoyl (or oleoyl or palmitoyl) taurines.

Linear molecularly dehydrated polyphosphate salts can be optionally employed herein as anticalculus agents in the form of their wholly or partially neutralized water soluble alkali metal (e.g. potassium or sodium) or ammonium salts, and any mixtures thereof. Representative examples include sodium tripolyphosphate, monosodium triacid-, disodium diacid-, trisodium monoacid-, and tetrasodium-pyrophosphates, the corresponding potassium salts and the like and are employed in the oral compositions in amounts of about 0.1 to about 3% by weight. Preferred anticalculus agents are tetraalkali metal pyrophosphates such as tetrasodium and tetrapotassium pyrophosphates, and mixtures thereof.

Fluoride ions may also be included in the oral compositions of the present invention to provide an anticaries effect. Among these materials are inorganic fluoride salts, such as soluble alkali metal fluoride salts, for example, sodium fluoride, potassium fluoride, sodium monofluorophosphate and sodium hexafluorosilicate. Alkali metal and tin fluorides, such as sodium and stannous fluorides, sodium monofluorophosphate and mixtures thereof, are preferred.

The amount of fluorine-providing salt is generally present in the oral composition at a concentration of about 0.0005 to about 3.0% by weight. Any suitable minimum amount of such salt may be used, but it is preferable to employ sufficient fluoride salt to release about 300 to 2,000 ppm.

In the aspect of this invention wherein the oral composition is a gel or paste, an orally acceptable vehicle, including a water-phase with humectant which is preferably glycerine or sorbitol or an alkylene glycol such as polyethylene glycol or propylene glycol is present, wherein water is present typically in an amount of about 15 to 40% by weight and glycerine, sorbitol and/or the alkylene glycol (preferably propylene glycol) typically total about 20 to about 75% by weight of the oral composition, more typically about 25 to about 60% by weight.

The dentifrice vehicle may contain a dentally acceptable abrasive material such as sodium bicarbonate or water insoluble abrasive material such as sodium metaphosphate, potassium metaphosphate, tricalcium phosphate, dihydrated dicalcium phosphate, anhydrous dicalcium phosphate, calcium pyrophosphate, calcium carbonate, aluminum silicate, hydrated alumina, calcined alumina, silica, bentonite, and mixtures thereof.

The abrasive material is generally present in the paste or gel composition in weight concentrations of about 10% to about 60% by weight, preferably about 10% to about 30% in a gel and about 25% to about 60% in a paste.

Toothpastes as well as gel dentifrices typically contain a natural or synthetic thickener or gelling agent in proportions of about 0.1 to about 10% by weight, preferably about 0.5 to about 5% by weight. Suitable thickeners or gelling agents include Irish moss, iota-carrageenan, kappa-carrageenan, gum tragacanth, starch, polyvinylpyrrolidone, hydroxyethyl propyl cellulose, hydroxybutyl methyl cellulose, hydroxypropyl methyl cellulose, hydroxyethyl cellulose and sodium carboxymethyl cellulose.

Natural or synthetic anionic polycarboxylates having a molecular weight of about 1,000 to about 5,000,000, preferably about 30,000 to about 500,000 may also be included in the oral composition. Synthetic anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl either/maleic anhydride having a molecular weight (M.W.) of about 30,000 to about 1,000,000, most preferably about 30,000 to about 500,000. These copolymers are available, for example, under the trade designation Gantrez AN 139 (M.W. 500,000), AN 119 (M.W. 250,000); and preferably Gantrez S-97 Pharmaceutical Grade (M.W. 70,000), of GAF Corporation.

Other anionic polycarboxylates useful in the practice of the present invention include the 1:1 copolymers of maleic anhydride with ethyl acrylate, hydroxyethyl methacrylate, N-vinyl-2-pyrollidone, or ethylene, the latter being available, for example, as Monsanto EMA No: 1103, M.W. 10,000 and Grade 61, and 1:1 copolymers of acrylic acid with methyl or hydroxyethyl methacrylate, methyl or ethyl acrylate, isobutyl methacrylate, isobutyl vinyl ether or N-vinyl-2-pyrrolidone.

Additional operative useful polycarboxylate compounds include copolymers of maleic anhydride with styrene, isobutylene or ethyl vinyl either, polyacrylic, polyitaconic and polymaleic acids, and sulfonacrylic oligomers of M.W. as low as 1,000 available under the trade designation Uniroyal ND-2.

Also useful in the practice of the present invention are the so-called carboxyvinyl polymers, commercially available, for example, under the trade designation Carbopol 934, 940 and 941 from B. F. Goodrich, these polymers consisting of a colloidally water-soluble polymer of polyacrylic acid crosslinked with from about 0.75% to about 2.0% of polyallyl sucrose or polyallyl pentaerythritol as a cross linking agent, often with M.W.'s up to 4–5 million or more.

The polycarboxylate compound, when employed, is incorporated in the oral compositions of the present invention in weight amounts of about 0.05 to about 5% by weight and preferably about 0.1 to about 3%.

Any suitable flavoring or sweetening material may also be employed. Examples of suitable flavoring constituents are flavoring oils, e.g. oil of spearmint, peppermint, wintergreen, sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine methyl ester, saccharine and the like. Suitably, flavor and sweetening agents may each or together comprise from about 0.1% to 5% or more of the preparation.

Agents used to diminish teeth sensitivity such as potassium chloride, potassium nitrate and potassium citrate can also be included in the oral compositions of the present invention at concentrations of about 0.1 about 10% by weight.

Various other materials may be incorporated in the oral compositions of this invention including whitening agents such as urea peroxide, hydrogen peroxide, preservatives, such as sodium benzoate, vitamins and chlorophyll compounds and desensitizing agents such as potassium chloride and potassium nitrate. These adjuvants, when present, are incorporated in the compositions in amounts which do not substantially adversely affect the properties and characteristics desired.

The oral compositions of the present invention may be prepared by suitably mixing the ingredients. For instance, in the preparation of a toothpaste or gel, the silver zeolite compound is dispersed in a mixture of ingredients, humectants, surfactants, thickener, abrasive and the stabilizing salt and flavor are then added and mixed. The ingredients are then mixed under vacuum for about 15–30 minutes. The resulting rinse product is then packaged. Dentifrices are prepared similarly, additional thickener and polishing agents being included in the last or penultimate step.

The compositions of this invention can be incorporated in lozenges, or in chewing gum or other products, e.g. by stirring into a warm gum base or coating the outer surface of a gum base, illustrative of which may be mentioned include jelutone, rubber latex and vinylite resins desirably with conventional plasticizers or softeners, sugar or other sweeteners or carbohydrates such as glucose, sorbitol and the like.

The vehicle or carrier in a tablet or lozenge is a non-cariogenic solid water-soluble polyhydric alcohol (polyol) such as mannitol, xylitol, sorbitol, malitol, a hydrogenated starch hydrozylate, hydrogenated glucose, hydrogenated disaccharides or hydrogenated polysaccharides, in an amount of about 90 to 98% by weight of the total composition. Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and Carbowax.

Lozenge formulations contain about 2% gum as a barrier agent to provide a shiny surface as opposed to a tablet which has a smooth finish. Suitable non-cariogenic gums include kappa carrageenan, carboxymethyl cellulose, hydroxyethyl cellulose, Gantrez, and the like.

The lozenge or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth.

The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

The following Examples further illustrate the present invention, but it is understood that the invention is not limited thereto. All amounts and proportions referred to herein and in the appended claims are by weight unless otherwise indicated.

EXAMPLE I

A dentifrice containing a silver zeolite antiplaque agent and a sodium chloride color stabilizing agent was prepared using the following ingredients:

| Ingredients | Weight % |
| --- | --- |
| Glycerin | 10.00 |
| Viscarin (gum) | 0.80 |
| Polyethylene glycol 600 | 1.00 |
| Sorbitol | 16.00 |
| Water | 15.69 |
| Saccharin | 0.20 |
| Sodium monofluorophosphate | 0.76 |
| TSPP | 0.25 |
| Sodium chloride | 0.30 |
| Titanium dioxide | 1.00 |
| Dicalcium phosphate dihydrate | 48.00 |
| Silver zeolite | 3.0* |
| Flavor | 1.00 |
| Sodium lauryl sulfate | 2.00 |
| Total | 100.00 |

*0.6% by weight as silver ion

The stability of the dentifrice of Example I was determined by an aging test in which the dentifrice is packaged in a sealed plastic tube and stored for at varying periods of time and temperatures.

The procedure of Example 1 (Ex. 1) was repeated except to prepare additional toothpaste compositions except that silver zeolite releasing 0.3% by weight silver ion was used and 0.3% by weight sodium citrate was used instead of 0.3% by weight NaCl as the stabilizing agent, designated toothpaste Ex. 2. In an additional toothpaste preparation, a silver zeolite releasing 0.3% silver ion in combination with 0.3% by weight NaCl was used, the toothpaste being designated toothpaste Ex. 3.

The toothpaste products were packaged in sealed plastic tubes and aged at varying times of 4–12 weeks at temperatures from room temperature (73° F.) to 120° F. The appearance of the toothpaste product was then evaluated for discoloration. The results of the aging tests are recorded in Table I below.

For purposes of comparison, the procedure of Example I was repeated except a toothpaste product designated "C" was prepared without the addition of a NaCl or calcium citrate stabilizing salt. For purposes of further comparison, the procedure of Example 1 was repeated except that the comparative toothpaste designated toothpaste C1 contained a silver zeolite which released 0.3% by weight silver and 0.3% by weight calcium carbonate. Those comparative toothpastes were also subjected to aging tests and the results of the comparative aging test are also recorded in Table I below.

TABLE I

| Tooth paste | Ingredients (by weight) | Aging Conditions | Discoloration (Browning) |
| --- | --- | --- | --- |
| Ex. 1 | 0.6% silver ion/0.3% NaCl | 12 wks. @ 73° F. | None |
| | | 12 wks. @ 105° F. | Very slight yellow |
| | | 12 wks. @ 120° F. | Slight yellow |
| Ex. 2 | 0.3% silver ion/0.3% calcium citrate | 4 wks. @ 73° F. | None |
| | | 4 wks. @ 105° F. | None |
| | | 4 wks. @ 120° F. | Very slight yellow |

TABLE I-continued

| Tooth paste | Ingredients (by weight) | Aging Conditions | Discoloration (Browning) |
|---|---|---|---|
| Ex. 3 | 0.3% silver ion/0.3% NaCl | 4 wks. @ 73° F.<br>4 wks. @ 105° F.<br>4 wks. @ 120° F. | None<br>None<br>None |
| C | 0.6% silver ion | 1 day @ 73° F. | Significant browning |
| C1 | 0.3% silver ion/0.3% CaCO$_3$ | 1 day @ 73° F. | Significant browning |

The results recorded in Table I indicate that only slight yellowing of the toothpaste compositions of the present invention (Ex. 1, 2 and 3) occurred at elevated temperatures after weeks of aging whereas significant browning of the comparative toothpaste (C, C1) occurred at room temperature after one day of aging at room temperature (73° F.).

Example II

To determine whether the presence of the sodium chloride stabilizing agent in a toothpaste containing silver zeolite had a negative impact on antiplaque efficacy, slurries of toothpastes of Example 1 were prepared which either contained both silver zeolite (0.3% by weight silver ion release) and 0.3% by weight sodium chloride (Ex. 4), or no silver zeolite (C-2) or silver zeolite (0.3% by weight silver ion release) without NaCl (C-3) in water by mixing one part by weight of toothpaste with 9 parts by weight of water.

Molten agar was mixed with a culture of *A. viscosus*. The toothpaste slurry was diluted from 1:10 to 1:320 in molten agar containing bacteria in doubling dilutions. Each concentration of toothpaste slurry was poured into appropriately marked petri dishes. The maximum inhibitory dilution (MID) is reported as the highest dilution that prevented bacterial growth, that is, the higher the inhibitory dilution, the more effective is the antibacterial agent. All MID determinations were performed in duplicate. The results are recorded in Table II below. TABLE II

TABLE II

| Toothpaste | MID |
|---|---|
| Ex. 4 | 1:160 |
| C-2 | 1:40 |
| C-3 | 1:80 |

The results recorded in Table II indicate no diminution of the antibacterial efficacy of the stabilized silver zeolite containing toothpaste of the present invention.

What is claimed is:

1. A method of stabilizing an oral composition containing silver zeolite as an antiplaque agent which comprises preparing a composition comprised of an orally acceptable vehicle and an effective amount of a silver zeolite, incorporating in the composition a color stabilizing amount of a slat selected from the group consisting of chloride, acetate and citrate salts, whereby the composition is stabilized during storage against discoloration by silver oxidation.

2. The method of claim 1 wherein the silver zeolite is present in the composition in an amount in the range of about 0.5 to about 5.0% by weight.

3. The method of claim 1 wherein the silver zeolite releases about 0.03 to about 3% by weight silver ion.

4. The method of claim 1 wherein the stabilizing chloride salt is sodium chloride.

5. The method of claim 1 wherein the stabilizing acetate salt is calcium acetate.

6. The method of claim 1 wherein the stabilizing acetate salt is calcium acetate.

7. The method of claim 1 wherein the stabilizing citrate salt is sodium citrate.

* * * * *